United States Patent [19]

Heise et al.

[11] Patent Number: 4,975,516

[45] Date of Patent: Dec. 4, 1990

[54] DIAMINOARYLSULFONES USEFUL FOR THE PREPARATION OF POLYURETHANE ELASTOMERS

[75] Inventors: Klaus-Peter Heise, Odenthal; Gerhard Grögler, Leverkusen; Karlfried Wedemeyer, Cologne; Dieter Dieterich, Leverkusen, all of Fed. Rep. of Germany

[73] Assignee: Bayer Aktiengesellschaft, Bayerwerk, Fed. Rep. of Germany

[21] Appl. No.: 295,635

[22] Filed: Jan. 10, 1989

[30] Foreign Application Priority Data

Jan. 16, 1988 [DE] Fed. Rep. of Germany ....... 3801083

[51] Int. Cl.$^5$ .................... C08G 18/32; C07C 321/00
[52] U.S. Cl. ......................................... 528/80; 528/64; 528/76; 564/340; 564/440
[58] Field of Search ................. 564/340, 440; 528/64, 528/80

[56] References Cited

U.S. PATENT DOCUMENTS

| | | | |
|---|---|---|---|
| 1,939,416 | 12/1933 | Schimmelschmidt et al. | 564/440 |
| 3,736,350 | 5/1973 | Meckel et al. | 260/471 |
| 4,152,510 | 5/1979 | Blahak et al. | 528/68 |
| 4,526,905 | 7/1985 | Lucast et al. | 528/64 |
| 4,529,746 | 7/1985 | Markovs et al. | 528/64 |
| 4,549,007 | 10/1985 | Lin et al. | 528/64 |
| 4,611,045 | 9/1986 | Ihrman | 528/64 |
| 4,613,704 | 9/1986 | Papenfuhs | 564/440 |

FOREIGN PATENT DOCUMENTS 2025896  7/1971  Fed. Rep. of Germany .

OTHER PUBLICATIONS

C. Hepburn, Polyurethane Elastomers, Applied Science Publishers Ltd., London, New York (1982), pp. 101 to 138.

*Primary Examiner*—John Kight, III
*Assistant Examiner*—Dennis R. Daley
*Attorney, Agent, or Firm*—Joseph C. Gil; Ricahrd E. L. Henderson

[57] ABSTRACT

This invention relates to diaminoarylsulfones of the formula

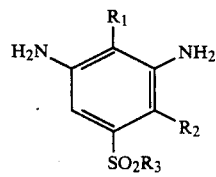

wherein $R_1$, $R_2$, and $R_3$ are independently $C_1$–$C_{12}$ alkyl, that are useful as chain extenders in the preparation of polyurethane elastomers.

5 Claims, No Drawings

DIAMINOARYLSULFONES USEFUL FOR THE PREPARATION OF POLYURETHANE ELASTOMERS

BACKGROUND OF THE INVENTION

The present invention relates to novel diaminoarylsulfones corresponding to formula (I)

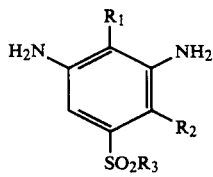

wherein $R_1$, $R_2$, and $R_3$ are independently $C_1$–$C_{12}$ alkyl. The present invention also relates to a process for the preparation of these new compounds and to their use.

Aromatic diamines play an important role in the production of polyurethane elastomers, enabling the use of tolylene diisocyanate ("TDI") prepolymers, which have a good storage stability and a suitable viscosity for casting.

The technically most important diamine is 3,3'-dichloro-4,4'-diaminodiphenylmethane ("MOCA") but it has certain disadvantages. Extensive efforts to find substitutes have therefore been made, and numerous products which can be reacted with TDI prepolymers to produce elastomers have subsequently become known. See, e.g., C. Hepburn, *Polyurethane Elastomers*, Applied Science Publishers Ltd., London, N.Y. (1982), pages 101 to 138.

Among these products, however, only 3,5-diamino-4-chlorobenzoic acid isobutyl ester (described in German Auslegeschrift 1,803,635) has achieved any practical importance. Like all the known slowly reacting diamines which give rise to high quality products, this compound has a symmetrical structure. This ester diamine combines excellent processing properties with a high level of quality in the elastomers obtained from it. Disadvantages of this compound include its relatively expensive method of preparation and, especially, the safety measures which are required for dinitration.

It has now surprisingly been found that the diaminoarylsulfones according to the present invention are well suited for use as diamine chain extending agents for the preparation of elastomers, especially when using the casting process. This suitability applies particularly to 1,3-diamino-2,4-dimethyl-5-methylsulfonylbenzene.

In DE-OS 2,001,772 and DE-OS 2,025,896 it has already been proposed to use 3,5-diamino-1-ethyl-sulfonyl-4-chlorobenzene as chain extender for the preparation of polyurethane ("PUR") elastomers. Halogenated sulfones of this type have, however, one serious disadvantage, both by comparison with the analogously structured halogenated benzoic acid esters and by comparison with the compounds according to this invention, in that they are very slow to react. Even at elevated temperatures, the residence time required in the mold is several hours. Moreover, the mechanical properties are only average, despite the symmetrical structure of the compound.

It must therefore be regarded as all the more surprising in the light of this state of the art that the sulfones according to the invention, which are asymmetric and free from chlorine atoms, not only provide advantageous processing properties and rapid hardening but also give rise to products with excellent mechanical properties.

The diaminoarylsulfones according to the invention result in PUR elastomers which have properties equal to those of the products according to DE-AS 1,803,635 but have the added advantages of being easier to prepare and, in particular, of requiring no special safety measures for the dinitration stage. The reactivity is somewhat higher than that of the above mentioned ester diamine, an advantage for a mechanical casting process and for the use of the product in the RIM process.

SUMMARY OF THE INVENTION

The present invention relates to novel alkyl-substituted aromatic diamines containing sulfone groups, in which each amino group is in a meta position relative to the sulfone group. The sulfone-group-containing aromatic diamines according to this invention correspond to formula (I)

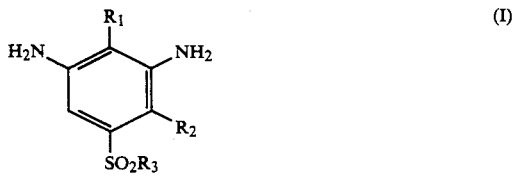

wherein $R_1$, $R_2$, and $R_3$ are independently $C_1$–$C_{12}$ alkyl, preferably $C_1$–$C_6$ alkyl. Compounds of formula (I) in which $R_1$ and $R_2$ are both methyl groups are particularly preferred.

The invention also relates to a process for the preparation of the novel compounds. The preparation of the new aromatic diamines containing sulfone groups may be carried out by a process similar to known processes. Thus, for example, diamines corresponding to the general formula (I) are obtained by dinitrating the corresponding sulfone precursors of formula (II)

wherein $R_1$, $R_2$ and $R_3$ have the same meaning as in formula (I), and then reducing the resulting compound using methods known in the art, such as catalytic hydrogenation or reduction with iron.

The present invention further relates to a process for the production of polyurethane elastomers from compounds in the molecular weight range of from about 800 to about 5,000 containing at least two hydroxyl groups, diisocyanates, and aromatic diamines as chain extenders wherein the chain extenders used are the diamines according to the invention corresponding to formula (I).

DETAILED DESCRIPTION OF THE INVENTION

The sulfone precursors corresponding to formula (II) are in part already known (e.g., 2,4-dimethyl-1-methylsulfonylbenzene) or may be obtained by known methods (for example, by the oxidation of sulfides or sulfoxides or by alkylation of the corresponding sulfinic acid salts). The preparation of sulfones is described, for example, in Houben Weyl, volume IX, 1955, on pages 227 to 241.

The following compounds exemplify the new sulfone-group-containing, alkyl-substituted aromatic diamines of formula (I):

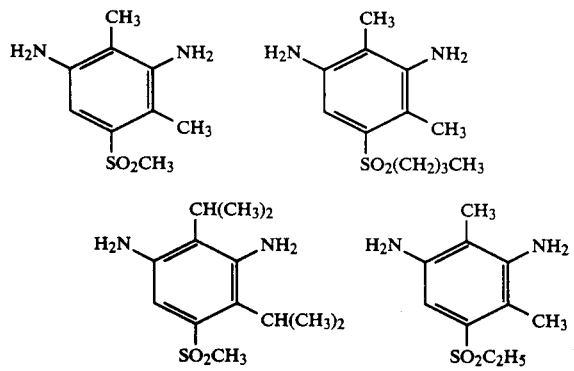

The compounds corresponding to formula (I) are particularly valuable as chain extenders in the production of synthetic resins with rubbery elastic properties by the known isocyanate polyaddition process.

In addition to the aromatic diamines according to the invention, the starting materials for the process for the production of polyurethane elastomers include compounds in the molecular weight range of from 800 to 5000, preferably from 1000 to 3000, containing at least two hydroxyl groups. Examples of such compounds include straight-chained or slightly branched polyesters containing hydroxyl groups which may be prepared by known methods from, for example, difunctional or higher functional alcohols and carboxylic acids or hydroxy carboxylic acids, and optionally with the addition of amino alcohols, diamines, oxyamines, or diamino alcohols. These polyesters may contain double- or triple-bonded unsaturated fatty acids. Straight-chained or slightly branched polyethers of the type obtained by the polymerization of alkylene oxides (such as ethylene oxide, propylene oxide, epichlorohydrin or tetrahydrofuran) or copolymers of this type may also be used. Straight-chained or branched addition products obtained by addition of the above-mentioned alkylene oxides to, for example, polyfunctional alcohols, amino alcohols, or amines are also suitable. Examples of suitable polyfunctional starting components for the addition of the alkylene oxides include ethylene glycol, 1,2-propylene glycol, 1,6-hexanediol, ethanolamine, and ethylene diamine. A proportion of trifunctional starting components, such as trimethylol propane or glycerol, may also be included. Mixtures of straight-chained and-/or slightly branched polyalkylene glycol ethers of various types may, of course, also be used.

The diisocyanates used as starting material according to the invention may be of any type known in the art. Examples of suitable diisocyanates include the aliphatic diisocyanates corresponding to the general formula OCN—(CH$_2$)$_n$—NCO wherein n is 2 to 8; cycloaliphatic diisocyanates, such as 2,4- and 2,6-hexahydrotolylene diisocyanate and mixtures of these isomers or dicyclohexylmethane diisocyanate; araliphatic diisocyanates, such as 1,3-xylylene diisocyanate; and aromatic diisocyanates, such as 2,4- and 2,6-tolylene diisocyanate and mixtures of these isomers. 1,4-Phenylene diisocyanate, 4,4'-diphenylmethane diisocyanate, 4,4'-diphenylether diisocyanate, and 1,5-naphthylene diisocyanate may also be used. According to the invention, isophorone diisocyanate and ester diisocyanates of carboxylic acids as described e.g., in British Patent Specification No. 965,474 may also be used as the diisocyanates. A proportion of triisocyanates may also be included.

The quantities of reactants are generally chosen so that the molar ratio of the diisocyanates to the total amount of chain extender plus compound containing reactive OH groups is generally from 1.0 to 1.5 (preferably from 1.05 to 1.25), depending on the particular process employed.

The molar ratio of NH$_2$ groups in the chain extender to reactive OH groups may vary within wide limits but should preferably be from 0.4 to 1.5, giving a range of products from soft to hard.

The process according to the invention for the production of polyurethanes may be carried out in various ways. For example, the compound containing at least two hydroxyl groups may be reacted with an excess of diisocyanate and, after the addition of chain extender, the resultant melt may then be poured into molds. A high quality elastic polyurethane resin is obtained at the end of several hours of after-heating.

According to another embodiment of the process, a mixture of the relatively high molecular weight compound containing at least two hydroxyl groups with the chain extender according to the invention is reacted with an excess of diisocyanate. The resultant reaction product is granulated and then molded under heat and pressure. The polyurethane resins obtained by this process may have various degrees of hardness and elasticity, depending on the proportions in which the reactants are used. It is possible by this method to obtain plastics which can be worked up thermoplastically. In another embodiment of the process, a mixture of the relatively high molecular weight compound containing at least two hydroxyl groups with the chain lengthening agent according to the invention is reacted with a subequivalent quantity of diisocyanate to produce a rollable sheet which may subsequently be converted into a rubbery elastic polyurethane (e.g., by crosslinking with an additional quantity of diisocyanate).

In the process according to the invention for the production of polyurethanes, the diamines of formula (I) wherein R$_1$, R$_2$ and R$_3$ are C$_1$-C$_6$ alkyl are preferred. Compounds of formula (I) in which R$_1$ and R$_2$ are methyl groups are particularly preferred as chain extenders. The compound 1,3-diamino-2,4-dimethyl-5-methylsulfonylbenzene is most preferred as chain extender.

The present invention, which is set forth in the foregoing disclosure, is not to be construed or limited either in spirit or in scope by these examples. Those skilled in the art will readily understand that known variations of the conditions and processes of the following preparative procedures can be used to prepare and use these compounds. In the following examples, all percentages are percentages by weight and all temperatures are degrees Celsius unless otherwise noted.

DESCRIPTION OF THE PREFERRED EMBODIMENTS

Preparation of Starting Compounds (a) 2,4-dimethyl-5-methylsulfonyl-1,3-dinitrobenzene 2,4-Dimethyl-1-methylsulfonylbenzene (138.5 g, 0.734 mol; 97.5% by gas chromatography ("GC"); Beilstein H 5, page 491) in 200 ml of sulfuric acid monohydrate was dinitrated with 118 g (1.83 mol) of 98% nitric acid. Half of the nitric acid is added dropwise at 20° to 30° C. with external cooling, and after the temperature is then allowed to rise to 70° C., the remaining quantity of nitric acid is added dropwise. After 30 minutes stirring at 70° C. following the addition of nitric acid, the reaction mixture is poured onto 700 ml of ice water, suction filtered, and washed sequentially with water, dilute sodium bicarbonate solution, and again water. Drying under vacuum leaves a residue of 180 g of the dinitro compound which according to GC contains less than 0.3% of mononitro compound.

Melting point 175° C. (toluene).

$^1$H-NMR (CDCl$_3$): δ(ppm) 2.53 (s, 3H, aromatic CH$_3$), 2.69 (s, 3H, aromatic CH$_3$), 3.17 (s, 3H, —SO$_2$—CH$_3$) and 8.65 (s, 1H, aromatic H).

(b) 2,4-dimethyl-5-ethylsulfonyl-1,3-dinitrobenzene

1-Ethylsulfonyl-2,4-dimethylbenzene (100 g, 0.5 mol; Beilstein H 5, page 491) is dinitrated with 83.6 g (1.3 mol) of 98% nitric acid by the method described above to yield 138 g of dinitro compound (92% of theoretical), 99.6% purity (GC).

Melting point (ethanol) 150° to 151° C.

(c) 2,4-dimethyl-5-propylsulfonyl-1,3-dinitrobenzene 2,4-Dimethyl-1-propylsulfonylbenzene (Beilstein H 5, page 491) was dinitrated analogously to (a).

Melting point 139° to 141° C.

$^1$-NMR (CDCl$_3$): δ(ppm) 1.07 (t, J=7 Hz, 3H, —CH$_2$—CH$_2$—CH$_3$), 1.80 (m, J=7 Hz, 2H, CH$_2$—CH$_2$—CH$_3$), 2.51 (s, 3H, aromatic CH$_3$), 2.67 (s, 3H, aromatic CH$_3$), 3.13 (m, 2H, —CH$_2$—CH$_2$—CH$_3$), and 8.58 (s, 1H, aromatic H).

(d) 5-isopropylsulfonyl-2,4-dimethyl-1,3-dinitrobenzene

1-Isopropylsulfonyl-2,4-dimethylbenzene was dinitrated analogously to (a).

Melting point 138.5° C. (ethanol).

$^1$H-NMR (DMSO-d$_6$): δ(ppm) 1.21 (d, J=7 Hz, 6H, —CH$_2$—(CH$_3$)$_2$), 2.45 and 2.60 (s each, 3H each and aromatic CH$_3$), 3.64 (m, J=7 Hz, 1H, —CH—(CH$_3$)$_2$), and 8.50 (s, 1H, aromatic H).

(e) 5-butylsulfonyl-2,4-dimethyl-1,3-dinitrobenzene

1-Butylsulfonyl-2,4-dimethylbenzene was dinitrated analogously to (a).

Melting point 116° to 118° C.

$^1$H-NMR (CDCl$_3$): δ(ppm) 0.94 (t, J=7 Hz, 3H, —CH$_2$—CH$_3$), 1.46 (6 lines, J=7 Hz, 2H, —CH$_2$—CH$_2$—CH$_2$—CH$_3$), 1.75 (m, 2H, —CH$_2$—CH$_2$—CH$_2$—CH$_3$), 2.52 (s, 3H, aromatic —CH$_3$), 2.67 (s, 3H, aromatic —CH$_3$), 3.16 (m, 3H, —CH$_2$—CH$_2$—CH$_2$—CH$_3$), and 8.58 (s, 1H, aromatic H).

(f) 2,4-diisopropyl-5-methylsulfonyl-1,3-dinitrobenzene 2,4-Diisopropyl-1-methylsulfonylbenzene was dinitrated analogously to (a). To ensure complete dinitration, 20% oleum (1.6 mol of SO$_3$ per mol of sulfone) was added after the addition of nitric acid and the after-stirring time was increased to 60 hours. The crude product was boiled with ethyl acetate to remove small quantities of mononitro compounds.

Melting point 214° to 215° C.

$^1$H-NMR (CDCl$_3$): δ(ppm) 1.33 and 1.37 (d each, J=7 Hz, 6H each, —CH—(CH$_3$)$_2$), 2.95 (m, J=7 Hz, 1H, —CH—(CH$_3$)$_2$), 3.18 (s, 3H, —SO$_2$—CH$_3$), 4.8 (broad, 1H, —CH—(CH$_3$)$_2$), and 8.25 (s, 1H, aromatic H).

EXAMPLE 1

1,3-diamino-2,4-dimethyl-5-methylsulfonylbenzene 2,4-Dimethyl-5-methylsulfonyl-1,3-dinitrobenzene (104 g, 0.379 mol) was hydrogenated in 150 ml of isopropyl alcohol in a 0.7 liter VA (steel) autoclave under a total pressure of 10 bar at 110° C. in the presence of 6 g of Raney nickel moistened with water. The catalyst is removed by filtration while hot. When the filtrate has cooled to room temperature, the diamine separates as crystals, yielding 69.2 g (85% of theoretical), 99.9% purity (GC).

Melting point (isopropyl alcohol) 131° C.

$^1$H-NMR (DMSO-d$_6$): δ(ppm) 1.90 (s, 3H, aromatic CH$_3$), 2.25 (s, 3H, aromatic CH$_3$), 3.01 (s, 3H, —SO$_2$—CH$_3$), 4.67 and 4.83 (s each, 2H each, —NH$_2$), and 6.63 (s, H, aromatic H).

Additional diamine was obtained from the mother liquor by evaporative concentration.

EXAMPLE 2

1,3-diamino-5-ethylsulfonyl-2,4-dimethylbenzene

1-Ethylsulfonyl-2,4-dimethyl-3,5-dinitrobenzene was hydrogenated to the diamine analogously to Example 1.

Melting point (ethanol) 155° C.

$^1$H-NMR (CCl$_4$): δ(ppm) 1.25 (t, J=7 Hz, 3H, —CH$_2$—CH$_3$), 2.02 (s, 3H, aromatic CH$_3$), 2.40 (s, 3H, aromatic CH$_3$), 3.00 (q, 2H, —CH$_2$—CH$_3$), 3.7 (broad, 4H, —NH$_2$), and 6.85 (s, 1H, aromatic H).

EXAMPLE 3

1,3-diamino-2,4-dimethyl-5-propylsulfonylbenzene 2,4-Dimethyl-1,3-dinitro-5-propylsulfonylbenzene was hydrogenated to the diamine analogously to Example 1.

Melting point (isopropyl alcohol) 159° to 160° C.

$^1$H-NMR (CDCl$_3$): δ(ppm) 0.98 (t, J=7 Hz, 3H, —CH$_2$—CH$_2$—CH$_3$), 1.72 (m, J=7 Hz, 2H, —CH$_2$—CH$_2$—CH$_3$). 2.02 (s, 3H, aromatic CH$_3$), 2.38 (s, 3H, aromatic CH$_3$), 3.02 (m, 2H, —CH$_2$—CH$_2$—CH$_3$), 3.62 and 3.72 (s each, broad, 2H each, —NH$_2$), and 6.84 (s, 1H, aromatic H).

EXAMPLE 4

1,3-diamino-5-isopropylsulfonyl-2,4-dimethylbenzene

1-Isopropylsulfonyl-2,4-dimethyl-2,5-dinitrobenzene was reduced to the diamine analogously to Example 1.

Melting point (isopropyl alcohol) 143.5° to 145° C.

$^1$H-NMR (CDCl$_3$): δ(ppm) 1.29 (d, J=7 Hz, 6H, —CH—(CH$_3$)$_2$), 2.04 (s, 3H, aromatic —CH$_3$), 2.40 (s, 3H, aromatic CH$_3$), 3.18 (7 lines, J=7 Hz, 1H, —CH—(CH$_3$)$_2$), 3.65 (s, broad, 4H, —NH$_2$), and 6.84 (s, 1H, aromatic H).

EXAMPLE 5

1,3-diamino-5-butylsulfonyl-2,4-dimethylbenzene

1-Butylsulfonyl-2,4-dimethyl-3,5-dinitrobenzene was reduced to the diamine analogously to Example 1.

Melting point (ethanol) 121° to 122° C.

$^1$H-NMR (CDCl$_3$): δ(ppm) 0.89 (t, J=7 Hz, 3H, —CH$_2$—CH$_3$), 1.36 (6 lines, J=7 Hz, 2H, —CH$_2$—CH$_3$), 1.66 (m, 2H, —CH$_2$—CH$_2$—CH$_2$—CH$_3$), 2.02 (s, 3H, aromatic CH$_3$), 2.40 (s, 3H, aromatic CH$_3$), 3.03 (m, 2H, —CH$_2$—CH$_2$—CH$_2$—CH$_3$), 3.58 (s, broad, 4H, —NH$_2$), and 6.84 (s, 1H, aromatic H).

EXAMPLE 6

1,3-diamino-2,4-diisopropyl-5-methylsulfonylbenzene 2,4-Diisopropyl-5-methylsulfonyl-1,3-dinitrobenzene was hydrogenated to the diamine analogously to Example 1.

Melting point (toluene) 164° to 165° C.

$^1$H-NMR (CDCl$_3$): δ(ppm) 1.38 (d, J=7 Hz, 6H, —CH—(CH$_3$)$_2$), 1.42 (d, J=7 Hz, 6H, —CH—(CH$_3$)$_2$), 3.02 (s, 3H, —SO$_2$—CH$_3$), 3.19 (m, J=7 Hz, 1H, —CH—(CH$_3$)$_2$), 3.65 and 3.90 (s, broad, 2H each, —NH$_2$), 4.04 (m, J=7 Hz, 1H, —CH—(CH$_3$)$_2$), and 6.78 (s, 1H, aromatic H).

EXAMPLES 7–11:

Preparation of Polyurethanes.

The diaminoalkylphenylsulfones listed in the following Table 1 were used in a casting process. In the examples given, the diamines were added in the molten form to a suitable polyadduct containing isocyanate end groups (i.e., an isocyanate prepolymer). The isocyanate prepolymer used in Examples 7–11 was an addition product prepared by a known process from 2.1 mol (365.4 g) of 2,4-diisocyanatotoluene ("TDI") and 1 mol (2,000 g) of a straight-chained polyester of adipic acid and ethylene glycol (OH number 56, molecular weight 2000) having an isocyanate content of 3.90%. For each example, 500 g of the said isocyanate prepolymer were degassed under aspirator vacuum at 80° C. for about 15 minutes before processing. The molten diamine was then added in the quantity required for complete reaction (i.e., equimolar) of the isocyanate groups of the prepolymer with the NH$_2$ groups of the diamine (NCO/NH$_2$ ratio=1:0). The casting time of the reaction mixtures at 70° to 80° C. is determined by the reactivity of the diamines according to the invention and, for practical purposes, generally lies within the range of 2 to 10 minutes. The reaction mixture is poured into a mold which has been treated with mold release agent and heated to about 100° C. The mixture is then heated for ½ to 4 hours at 120° C. After removal from the mold (½ to 1 hour) the PUR elastomers were tempered for 10 to 12 hours at 120° C.

Table 1 gives a summary of the casting time of the reaction mixtures and the mechanical properties of the elastomers obtained using the diamines according to the invention.

TABLE 1

| Example | 7 | 8 | 9 | 10 | 11 |
|---|---|---|---|---|---|
| R$_1$ | CH$_3$ | CH$_3$ | CH$_3$ | CH$_3$ | CH$_3$ |
| R$_2$ | CH$_3$ | CH$_3$ | CH$_3$ | CH$_3$ | CH$_3$ |
| R$_3$ | CH$_3$ | C$_2$H$_5$ | C$_3$H$_7$ | CH(CH$_3$)$_2$ | C$_4$H$_9$ |
| Quantity (g per 500 g of NCO prepolymer) | 49.7 | 52.6 | 57.6 | 56.2 | 59.4 |
| Casting time (min) | 4 | 5 | 3 | 6 | 6 |
| Modulus 100% (MPa) | 6.2 | 5.1 | 4.2 | 2.2 | 4.5 |
| Tensile strength (MPa) | 37.7 | 27.8 | 20.0 | 17.6 | 21.4 |
| Elongation at break (%) | 652 | 650 | 650 | 550 | 700 |
| Tear propagation resistance (KN/m) | 75.0 | 65.2 | 26.0 | 57.8 | 61.1 |
| Shore A hardness | 86 | 85 | 84 | 78 | 82 |
| Elasticity (%) | 34 | 27 | 25 | 23 | 27 |

EXAMPLE 12

(comparison; not according to the invention)

Molten 3,5-diamino-1-ethylsulfonyl-4-chlorobenzene (54.4 g) corresponding to the following formula

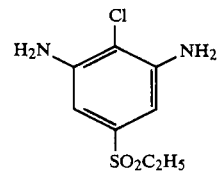

was added to 500 g of the isocyanate prepolymer described above (Examples 7 to 11) having an isocyanate content of 3.9%. The polyurethane elastomer was produced under the same operating conditions as mentioned above but the reaction mixture solidifies quite differently from those used in experiments previously described. Reaction of the diamine with the isocyanate groups of the prepolymer takes place very slowly at a reaction temperature of 70° to 80° C. The casting for the reaction mixture is performed at about 45° to 60° C. However, the solidification time of the liquid reaction mixture at 120° C. is also very long, so that it is only after several hours (3 to 5 hours) that the products can be removed from their mold. In contrast, in the experimental batches described above in Examples 7 to 11, the mold release time is only 15 to 60 minutes, so that the two components can be worked up very rapidly.

A polyurethane(urea) elastomer having the following mechanical properties is obtained:

| | |
|---|---|
| Modulus at 100%: | 2.9 MPa |
| Tensile strength: | 17.9 MPa |
| Elongation at break: | 650% |
| Tear propagation resistance: | 37 KN/m |
| Shore A hardness: | 83 |
| Elasticity: | 21% |

What is claimed is:

1. A compound having the formula

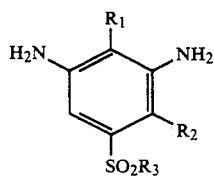

wherein $R_1$, $R_2$, and $R_3$ are independently $C_1$-$C_{12}$ alkyl.

2. A compound according to claim 1 wherein $R_1$, $R_2$, and $R_3$ are independently $C_1$-$C_6$ alkyl.

3. A compound according to claim 1 wherein $R_1$ and $R_2$ are methyl.

4. A compound according to claim 1 selected from the group consisting of

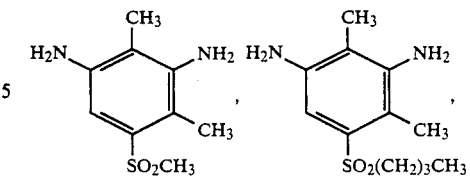

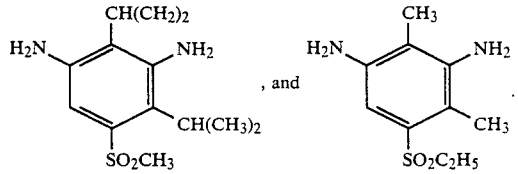

5. A method of preparing a polyurethane elastomer comprising reacting a mixture of one or more diisocyanates, one or more compounds having a molecular weight of from about 800 to about 5,000 and containing at least two hydroxyl groups, and a compound according to claim 1 as chain extender.

* * * * *